United States Patent
Izvoztchikov et al.

(10) Patent No.: US 6,902,928 B2
(45) Date of Patent: Jun. 7, 2005

(54) TREATMENT COMPARTMENT FOR TREATING HISTOLOGICAL SAMPLES

(75) Inventors: Ilia Borisovitch Izvoztchikov, St. Petersburg (RU); Helge Ebeling, Bechtheim (DE)

(73) Assignee: Microm International GmbH, Walldorf (DE)

( * ) Notice: Subject to any disclaimer, the term of this patent is extended or adjusted under 35 U.S.C. 154(b) by 0 days.

(21) Appl. No.: 10/476,454

(22) PCT Filed: Dec. 11, 2002

(86) PCT No.: PCT/EP02/14040

§ 371 (c)(1),
(2), (4) Date: Oct. 31, 2003

(87) PCT Pub. No.: WO03/054520

PCT Pub. Date: Jul. 3, 2003

(65) Prior Publication Data

US 2004/0137609 A1 Jul. 15, 2004

(30) Foreign Application Priority Data

Dec. 21, 2001 (DE) .......................... 101 63 487

(51) Int. Cl.⁷ ................................. H01N 1/00
(52) U.S. Cl. ............... 435/284.1; 435/286.5; 435/307.1; 422/224; 422/228; 422/292; 422/300
(58) Field of Search ............... 422/207, 224, 422/228, 292, 300; 435/284.1, 286.5, 307.1

(56) References Cited

U.S. PATENT DOCUMENTS 3,435,835 A  4/1969  Hobbs
4,353,381 A  10/1982 Winters
4,358,470 A  11/1982 Rasmussen
4,576,796 A  3/1986  Mccormick
5,316,945 A  5/1994  Minuth
6,413,767 B1 * 7/2002 Izvoztchikov et al. ... 435/286.5

FOREIGN PATENT DOCUMENTS

| EP | 0 856 729 | 8/1998 |
| EP | 0 969 277 | 1/2000 |
| RU | 2 083 163 | 10/1997 |
| WO | WO 96 29 866 | 10/1996 |

* cited by examiner

Primary Examiner—David A. Redding
(74) Attorney, Agent, or Firm—Paul Vincent

(57) ABSTRACT

The invention relates to a treatment compartment (1) for treating histological samples with treating agents (2, 2', 2"). The treatment compartment (1) comprises a housing (3) with an inlet and outlet (4, 4') for the treating agents (2, 2', 2"), a rotatable retaining device (5) which receives the samples and a closable access opening (6) on the front (7). The aim of the invention is to improve a treatment compartment (1) of the above kind in such a way that it has a compact design and is easily accessible without the risk of the treating agents (2, 2', 2") emerging. According to the invention, the housing (3) is designed and mounted in such a manner and at least the lower zone of the front (7) is provided with such a rim (8) that a liquid level (9) of the treating agents (2, 2', 2") can be formed even when the access opening (6) is open, and that the sample is held in the retaining device (5) in such a way that it can be moved, when the retaining device rotates, through the treating agents (2, 2', 2") forming the liquid level (9).

15 Claims, 3 Drawing Sheets

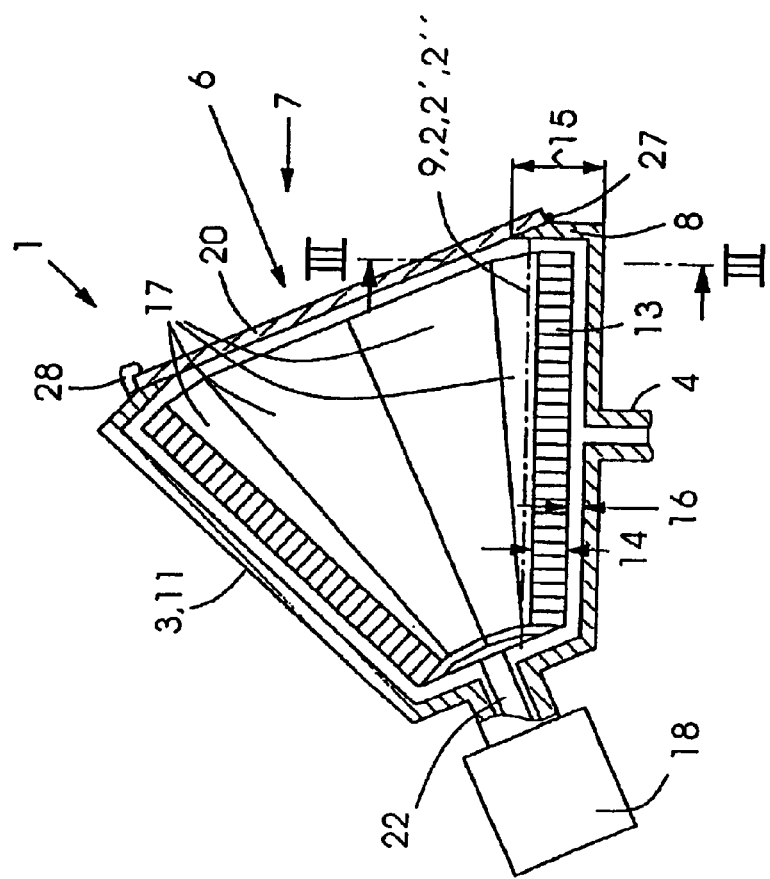

TREATMENT COMPARTMENT FOR TREATING HISTOLOGICAL SAMPLES

This application is the national stage of PCT/EP02/14040 filed on Dec. 11, 2002 and also claims Paris Convention priority of DE 101 63 487.0 filed on Dec. 21, 2001.

BACKGROUND OF THE INVENTION

The invention concerns a treatment chamber for the treatment of histological samples with treatment agents, wherein the treatment chamber has a housing with a supply and discharge for treatment agents, a rotatable holding means for receiving the samples, and a closable access opening on the front side.

Devices comprising such treatment chambers are provided for the treatment of histological samples for microscopic examinations wherein the samples to be examined are subjected to a series of sequential processing steps, such as e.g. fixation, e.g. in an aqueous formaldehyde solution, dehydration, clearing and infiltration with paraffin or another suitable wax. For dehydration, the fixed samples are treated with alcohol reagents with gradually increasing concentration. For clearing, the dehydrated samples are treated once or several times with a clearing agent, e.g. xylol. The latter is an intermediate medium, which removes alcohol and subsequently introduces paraffin, since direct replacement of alcohol by paraffin is not possible. The clearing also improves the contrast. For infiltration with paraffin (or another wax), the dehydrated and cleared samples are also immersed several times into molten paraffin or another molten wax. Only then is the histological sample suitable for processing with a microtome. Thin sections are thereby produced which can be investigated under a microscope.

A treatment chamber of the above-mentioned type is disclosed in RU 99 12 63 11 A1 (Abstract, claim 13). To ensure that such a treatment chamber can also be opened without discharging treatment agent—which may be the current charge or residual amounts—this document suggests designing the treatment chamber to be pivotable such that the door opens from above. This solution requires substantial technical effort and accessibility of the treatment chamber from above is not optimal.

It is therefore the underlying purpose of the present invention to design a treatment chamber such that it can be easily accessed and has a simple construction without the danger of leaking treatment agent.

SUMMARY OF THE INVENTION

This object is achieved in accordance with the invention in that the housing has an edge at least in the lower region of the front side and is designed and disposed accordingly in such a manner that even when the access opening is open, a liquid level of treatment agents is maintained, wherein the holding means has a sample arrangement which can rotate through the treatment agent defining the liquid level.

The invention is advantageous in that the treatment chamber is designed with simple means such that it can be opened at any time when stopped without the danger that treatment agent exits even if it is filled to a maximum level thereof. In this fashion, it is almost impossible to open the treatment chamber at the wrong time, leading to discharge of treatment agent, and samples can be removed or recharged even when the treatment chamber is filled with treatment agent. Moreover, the opening of the treatment chamber on the front side, which does not assume the horizontal position of prior art, provides optimum accessibility for the samples to the holding means to permit easy removal or recharge of samples or containers containing samples at any time.

The treatment chamber can be formed in different ways. It is possible to form the housing as a horizontally disposed cylinder and form the holding means such that it guides the samples on circular paths along the inner cylinder walls, wherein the edge projects beyond the samples which are located at the lowest point of the circular path.

In a further embodiment, the housing is formed as a truncated cone which is disposed such that the lowest tangent line thereto extends horizontally, and the holding means is designed such that it guides the samples on circular paths along the inner truncated cone wall, wherein the edge is disposed on the large circular surface of the truncated cone such that it projects beyond those samples located at the lowest points.

The advantages mentioned above are guaranteed by both embodiments. The truncated cone design has the additional advantage that the access opening is located on the large circular surface, which is upwardly inclined. A large opening with ergonomically optimum orientation and accessibility to the entire housing is thereby produced.

Cassettes containing the sample can preferably be arranged in the holding means such that they extend substantially along the entire inner wall of the housing, having a thickness, in conjunction with the holding means and its play, which is smaller than the width of the edge. In consequence thereof, the liquid level in the housing must not be excessively high in order to wet all samples located on the holding means during rotation thereof. In this manner, consumption of treatment agent is very small, i.e. optimum. Optimum results are achieved when only one layer of cassettes is provided.

The holding means is preferably designed to receive containers in which several cassettes can be arranged. This permits supply of cassettes to these containers outside of the treatment chamber, introduction of these containers into the treatment chamber, and connection thereof to the holding means.

When the housing is designed as truncated cone, a very simple and inexpensive production method consists of shaping the housing from one single piece of sheet metal. Since in this embodiment, the holding means for the samples or containers holding the samples also has the shape of a truncated cone, it can also be economically produced by shaping one single piece of sheet metal. Conventional welding work required for producing the corresponding conventional cylinders is unnecessary. The production from one single piece of sheet metal through pressurization is particularly economical.

The treatment chamber preferably has a drive which is connected to a control for supply and discharge of treatment agent and for rotating the holding means until the samples are sufficiently wetted for the respective treatment step.

Since opening the door to the access opening while the holding means rotates could cause leakage of treatment agent, it is preferable to design the control such that it opens the door only when the drive for the holding means is at rest.

Treatment chambers must be provided with an explosion protection for treatment with certain agents. Towards this end, the European Standard EN 600 79-10 demands encapsulation of the region at risk. It is therefore proposed that an explosion-proof jacket surrounds the holding means. The jacket is therefore relatively small and must not surround a large part of the device or the entire device. To prevent interruption of this encapsulation, it is proposed that the drive acts on the holding means through the explosion-proof jacket via a magnet carrier. Of course, the holding means must be rotatably disposed in the explosion-proof jacket.

BRIEF DESCRIPTION OF THE DRAWING

The invention is explained below with reference to embodiments shown in the drawing.

FIG. 3 shows a further embodiment of the invention;

FIG. 4 shows a section through this further embodiment; and

DESCRIPTION OF THE PREFERRED EMBODIMENT

Figure 1:
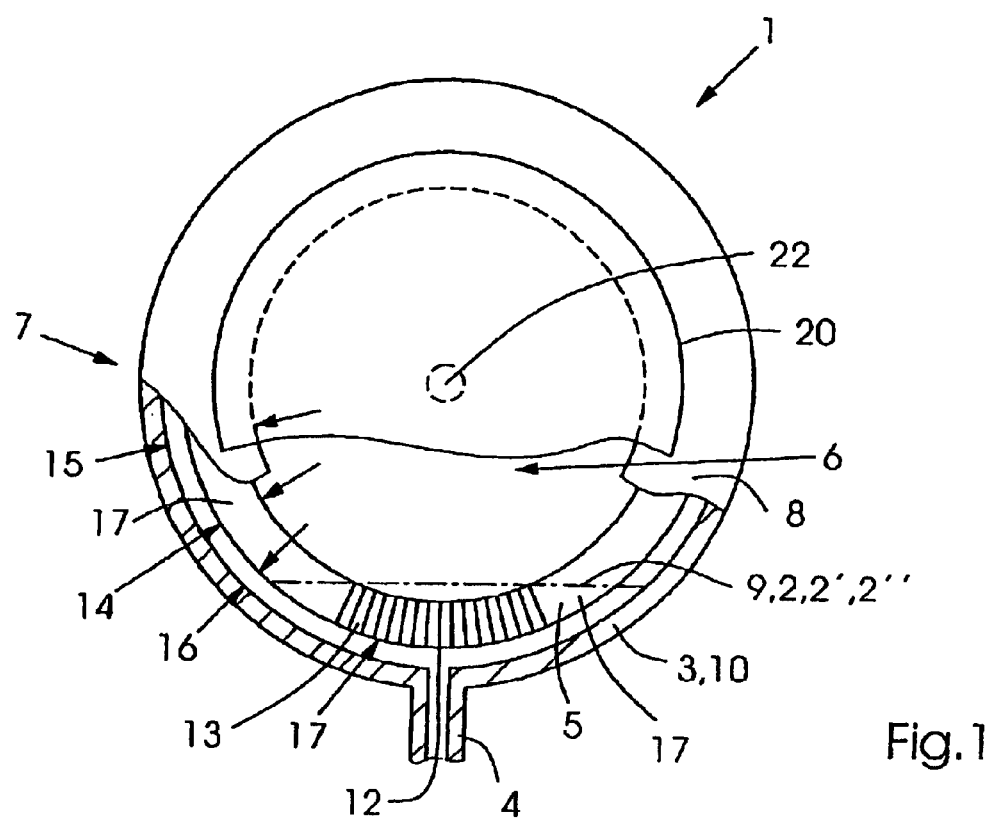
FIG. 1 shows a first embodiment of the invention.

FIG. 1 shows a first embodiment of the invention wherein the treatment chamber 1 has a housing 3 which is formed as cylinder 10. This cylinder 10 is disposed horizontally with the lowermost tangent line 12 thereto being the lowest point. The delivery and discharge 4 for treatment agent 2, 2', 2" is also located there. A holding means 5 for receiving samples is located in the housing 3 which has a cylindrical shape such that containers 17 for cassettes 13 which carry the samples extend along the inner wall of the housing 3. The cassettes 13 are thereby preferably disposed in a single layer, such that a relatively low liquid level 9 (dash-dotted line) of a treatment agent 2, 2' or 2" is sufficient for wetting all cassettes 13 when the holding means 5 turns. An axle 22 is disposed on the holding means 5 for this rotation and guided through the housing 3 to a drive 18. The cassettes 13 are indicated only in the lowest container 17 for reasons of clarity.

The front side 7 of the treatment chamber 1 has an access opening 6 which can be closed by a door 20. To prevent leakage of treatment liquid 2, 2' or 2", when the door 20 is opened, even when the liquid level 9 has been fully reached, an edge 8 is provided having a width 15 which is larger than the thickness 14 of the sample arrangement on the holding means 5 plus the play 16 of the holding means 5 relative to the inner wall of the housing 3. In this fashion, the door 20 can always be opened when the drive 18 has stopped, even when the treatment liquid 2, 2' or 2" has reached the liquid level 9. The edge 8 is broken away (as is part of the door 20) in the lower region to show the inside of the treatment chamber 1.

Figure 2:
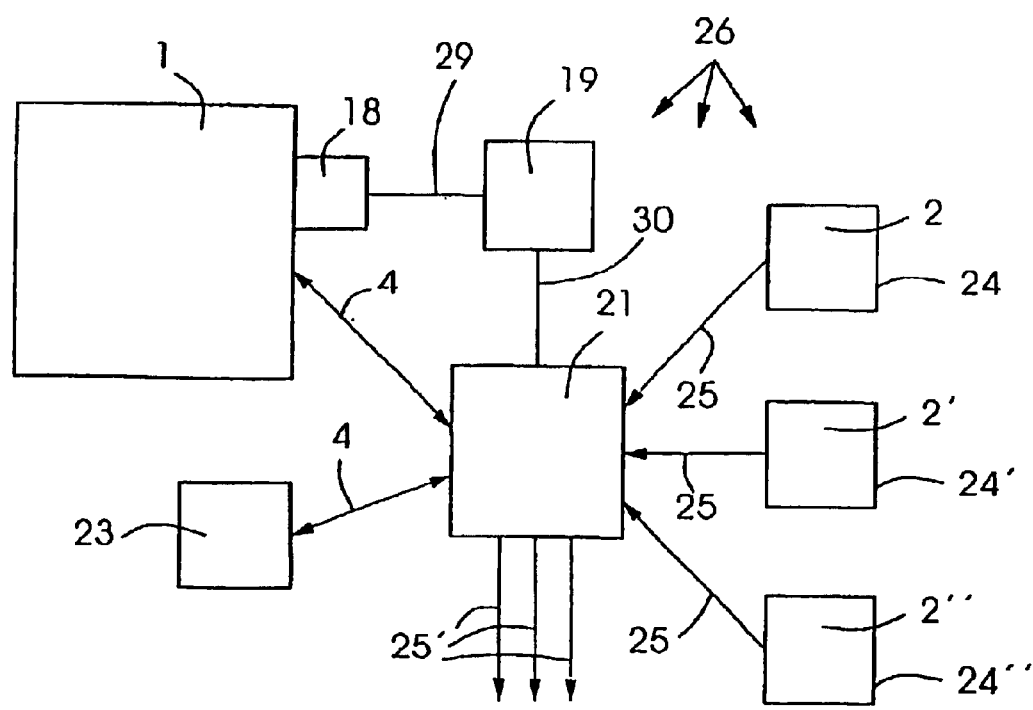
FIG. 2 shows insertion of a treatment chamber into the overall device to treat histological samples.

FIG. 2 shows the arrangement of a treatment chamber of the inventive type in the overall device 31 for treating histological samples. It can be used for one treatment chamber 1 and also for further treatment chambers 23. A further treatment chamber 23 may be smaller to carry out brief treatment of smaller amounts. The entire device 31 has a control 19 which actuates the drive 18 via a connecting line 29 and a means 26 for supply and discharge of treatment agent 2, 2', 2" via a connecting line 30. Towards this end, a valve unit 21 is arranged which receives treatment agent 2, 2', 2" via supplies 25. It can be stored in supply containers 24, 24', 24". The number of treatment agents 2, 2', 2" is shown by way of example only; it may be larger depending on the number of treatments to be carried out. The valve unit 21 is connected to the supply and discharge 4 of the treatment chamber 1 or a further treatment chamber 23 and serves as supply and discharge of treatment agent 2, 2', 2".

Discharge lines 25' discharge used treatment agent which is preferably discharged separately to permit recycling.

FIG. 3 shows a further embodiment of the invention with a housing 3 which has the shape of a truncated cone 11. The lower region of the front side 7 is broken away to show the holding means 5 for receiving containers 17 for cassettes 13 on which the samples are disposed. To illustrate the design in detail, FIG. 4 shows a section indicated in FIG. 3 with IV—IV. The partial section of FIG. 3 is indicated in FIG. 4 with III—III.

As can be gathered from the two illustrations, the housing 3 and also the holding means 5 have the shape of a truncated cone. The latter extends with play 16 along the inner wall of the housing 3, 11. The housing 3, formed as truncated cone 11, is disposed such that its tangent line is horizontal. The supply and discharge 4 for treatment agent 2, 2', 2" are also disposed there. For this embodiment of the housing 3 as a truncated cone 11, a relatively low liquid level 9 is sufficient to wet all samples by turning the holding means 5. This embodiment of the treatment chamber 1 also has an edge 8 of width 15 which exceeds the thickness 14 of the sample arrangement plus play 16. In this fashion, the door 20 can be opened when completely filled with treatment agent 2, 2' or 2" to the liquid level 9 without leakage of treatment agent 2, 2' or 2". Towards this end, the drive 18, which is disposed on the small circular surface of the truncated cone 11 and connected to an axle 22 and to holding means 5, should be stopped.

In this embodiment, the containers 17 for receiving the cassettes 13 are disposed like a conical jacket on the holding means 5 producing mainly trapezoidal shapes of the containers 17. In this case as well, only one layer of cassettes 13 are preferably disposed to guarantee economical consumption of treatment agent 2, 2', 2" with a low liquid level 9. The door 20 can be opened by a hinge 27 and safely closed by a lock 28. The latter can be blocked by the control 19 when the drive 18 and therefore the holding means 5 still rotate to prevent treatment agent 2, 2' or 2" from being discharged when opening during operation.

This embodiment of the invention is advantageous in that the truncated conical design of the housing 3, 11 permits provision of a very large access opening 6 which additionally has an ergonomically very favourable access position. This greatly optimises the accessibility and ensures rapid access to all samples. Since the door 20 can also be opened when treatment agent 2, 2', 2" is filled in, permanent removal or adding of samples is thereby possible.

Figure 5:
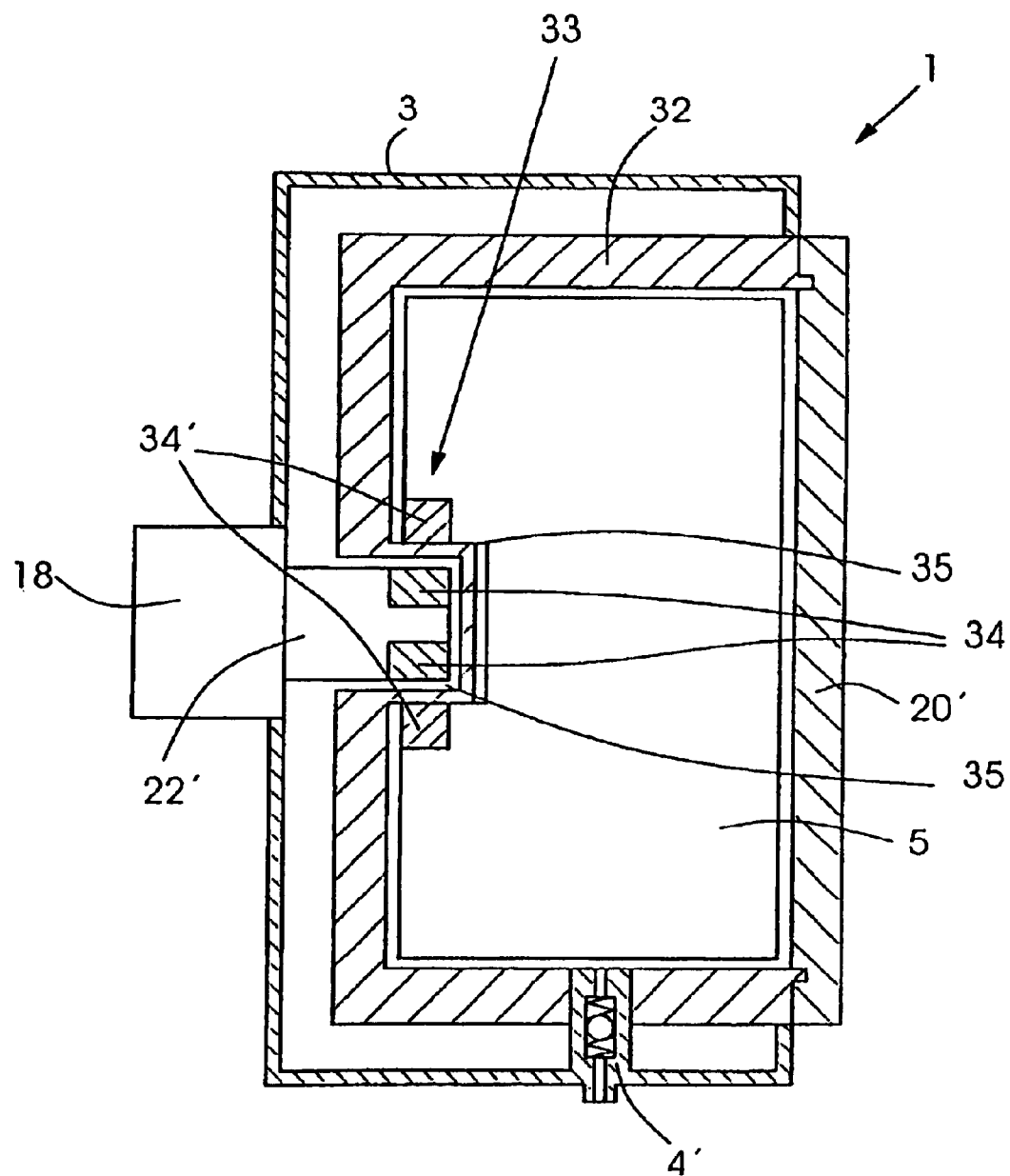
FIG. 5 shows a basic representation of an embodiment with an explosion-proof jacket.

FIG. 5 shows a basic illustration of an embodiment with an explosion-proof jacket 32. It is disposed in the housing 3 and surrounds the holding means 5 as complete encapsulation. The housing 3 is shown symbolically, it usually comprises further device parts (see FIG. 2). Since the jacket 32 should have no interruptions, the drive 18 has an axle 22' having magnets 34 at its front side which carry along the holding means 5, also provided with magnets 34', through the jacket 32. The holding means 5 has a bearing 35 which may be disposed e.g. in the region of this magnet carrier 33. The explosion-proof jacket 32 must also comprise an explosion-proof door 20' and an explosion-proof supply and discharge 4' for treatment agent 2, 2', 2".

The embodiments are of course only exemplary, and treatment chambers 1 with the most different of rotationally symmetrical shapes are also feasible. The holding means 5, which is merely symbolically shown by the arrangement of the containers 17, can be designed in the most different of ways. Feasible are cages or perforated sheet metal cages, which are formed corresponding to the respective shape of the housing 3, with receptacles for the container 17 holder. Star-shaped designs for hanging containers 17 to the ends of the arms are also feasible.

Treatment Chamber for Treatment of Histological Samples
List of Reference Numerals
1 Treatment chamber
2,2',2" Treatment agent
3 Housing
4,4' Supply and discharge for treatment agent
5 Holding means for receiving samples
6 Access opening
7 Front side of treatment chamber
8 Edge
9 Liquid level
10 Cylinder (housing)
11 Truncated cone (housing)
12 Lowermost tangent line
13 Cassettes for samples
14 Thickness of sample arrangement
15 Width of edge
16 Play
17 Containers for cassettes
18 Drive
19 Control
20,20' Door for closing the access opening
21 Valve unit
22,22' Axle of holding means
23 Further treatment chamber
24,24',24" Supply container for treatment agent
25,25' Lines for treatment agent
25 Supply to valve unit
25' Disposal
26 Means for supply and discharge of treatment agent
27 Hinge
28 Lock
29 Connecting line between control and drive
30 Connecting line between control and valve unit
31 Overall device for treatment of histological samples
32 Explosion-proof jacket
33 Magnet carrier
34,34' Magnets
35 Storage

We claim:

1. A device for treatment of histological samples with a treatment agent, the device comprising:
 a housing having a supply and a discharge for the treatment agent, said housing also having an access opening on a front side thereof and an edge disposed at least in a lower region of said front side;
 means for closing said access opening through cooperation with said housing; and
 a sample holding means disposed for rotation within said housing, said holding means arranging the samples to rotate through a liquid level defined by the treatment agent, wherein said edge is structured and disposed to partially obscure the access opening in order to maintain the liquid level of treatment agent even when said access opening is not closed.

2. The device of claim 1, wherein said housing is formed as a horizontally disposed cylinder and said holding means is structured and disposed to move samples through a substantially circular path along an inner cylindrical wall of said housing, wherein said edge projects past those samples which are located on a lowermost point of said circular path.

3. The device of claim 1, wherein said housing is formed as a truncated cone which is disposed such that a lowermost tangent line thereof extends horizontally, wherein said holding means is structured and disposed to guide the samples through a substantially circular path along an inner truncated cone wall, wherein said edge is disposed on a large circular surface of said truncated cone to project beyond those samples which are located at lowermost points of said circular path.

4. The device of claim 1, wherein said holding means comprises cassettes in which the samples are disposed, said cassettes extending substantially along an entire inner wall of said housing, wherein said edge has a width which exceeds a sum of a cassette plus holding means thickness and a clearance separation between said holding means and said housing.

5. The device of claim 4, wherein only one layer of cassettes is provided.

6. The device of claim 1, wherein said holding means is structured to receive containers in which several cassettes can be arranged.

7. The device or claim 3, wherein said housing is produced through shaping of one single piece of sheet metal.

8. The device of claim 3, wherein said holding means also has a shape of a truncated cone.

9. The device of claim 8, wherein said holding means is produced through shaping one single piece of sheet metal.

10. The device of claim 7, wherein production is effected through pressing.

11. The device of claim 9, wherein production is effected through pressing.

12. The device of claim 1, further comprising a drive connected to a control for delivery and discharge of treatment agents and for turning said holding means until the samples are sufficiently wetted for a respective treatment step.

13. The device of claim 12, wherein said control releases said means for closing said access opening only when said drive for said holding means is stopped.

14. The device of claim 1, further comprising an explosion-proof jacket surrounding said holding means.

15. The device of claim 14, wherein said drive acts on said holding means through said explosion-proof jacket via a magnet carrier.

* * * * *